United States Patent [19]
Carl

[11] Patent Number: 5,261,911
[45] Date of Patent: Nov. 16, 1993

[54] ANTEROLATERAL SPINAL FIXATION SYSTEM

[76] Inventor: Allen Carl, 308 Highgate Dr., Slingerlands, N.Y. 12159

[21] Appl. No.: 911,105

[22] Filed: Jul. 9, 1992

Related U.S. Application Data

[62] Division of Ser. No. 717,147, Jun. 18, 1991, Pat. No. 5,152,303.

[51] Int. Cl.⁵ .............................................. A61F 5/04
[52] U.S. Cl. ....................................... 606/61; 606/62
[58] Field of Search ....................... 606/60, 61, 62, 64, 606/72, 73

[56] References Cited

U.S. PATENT DOCUMENTS

| | | | |
|---|---|---|---|
| 3,648,691 | 3/1972 | Lumb et al. | 606/61 |
| 3,693,616 | 9/1972 | Roaf et al. | 606/61 |
| 3,867,728 | 2/1975 | Stubstad et al. | |
| 4,047,524 | 9/1977 | Hall | |
| 4,085,744 | 4/1978 | Lewis et al. | |
| 4,349,921 | 9/1982 | Kuntz | |
| 4,361,141 | 11/1982 | Tanner | |
| 4,422,451 | 12/1983 | Kalamchi | |
| 4,433,677 | 2/1984 | Ulrich et al. | |
| 4,448,191 | 5/1984 | Rodnyansky et al. | 606/61 |
| 4,569,338 | 2/1986 | Edwards | 606/61 X |
| 4,611,581 | 9/1986 | Steffee | |
| 4,636,217 | 1/1987 | Ogilvie et al. | |
| 4,655,199 | 4/1987 | Steffee | |
| 4,696,290 | 9/1987 | Steffee | |
| 4,743,260 | 5/1988 | Burton | |
| 4,773,402 | 9/1988 | Asher et al. | 606/61 |
| 4,790,297 | 12/1988 | Luque | |
| 4,836,196 | 6/1989 | Park et al. | |
| 4,878,915 | 11/1989 | Brantigan | 606/61 X |
| 4,913,134 | 4/1990 | Luque | |
| 4,950,269 | 8/1990 | Gaines, Jr. | |
| 5,000,165 | 3/1991 | Watanabe | 606/61 X |
| 5,005,562 | 4/1991 | Cotrel | 606/61 X |
| 5,042,982 | 8/1991 | Harms et al. | 606/61 |
| 5,067,955 | 11/1991 | Cotrel | 606/61 |
| 5,084,049 | 1/1992 | Asher et al. | 606/61 |
| 5,092,867 | 3/1992 | Harms et al. | 606/61 |
| 5,092,893 | 3/1992 | Smith | 606/61 X |
| 5,112,332 | 5/1992 | Cozad et al. | 606/61 |
| 5,129,900 | 7/1992 | Asher et al. | 606/61 |
| 5,133,716 | 7/1992 | Plaza | 606/61 |
| 5,147,359 | 9/1992 | Cozad et al. | 606/61 |

FOREIGN PATENT DOCUMENTS 9119469 12/1991 World Int. Prop. O. ............ 606/61

OTHER PUBLICATIONS

"Fixation of the Anterior Spondilodesis in Case of Thoracolumbar Spine Fractures", by G. H. Slot.
"Kaneda Anterior Spinal Instrumentation Systems", AcroMed Corporation, spec sheet.
"Early Clinical Experience with the Syracuse I-Plate: An Anterior Spinal Fixation Device", Yuan et al., 1987.
"Experience of Anterior Correction of Scoliosis", Dwyer, 1973.

(List continued on next page.)

Primary Examiner—Robert Bahr
Assistant Examiner—Linda C. M. Dvorak
Attorney, Agent, or Firm—Nixon & Vanderhye

[57] ABSTRACT

In accordance with one exemplary embodiment of the invention, an anterolateral rod fixation device includes a pair of rods which can be fixed in substantially parallel relationship to the anterolateral vertebral body by cannulated fixation screws and associated locking screws. Upper or lower ends of the rods are provided with vertical slots to facilitate independent screw placement, and to permit relative movement between the rods and fixation screws upon removal of the locking screws. A pair of cross links are provided for rigid interconnection between the rods. Thus, in accordance with one aspect of the invention, there is provided an anterolateral spinal fixation system comprising a pair of substantially parallel fixation members, each provided with means for enabling varied fixation screw placement; a pair of cross links extending between the parallel fixation members; the cross links extending through slots provided in the parallel fixation members and rigidly secured therein.

18 Claims, 3 Drawing Sheets

OTHER PUBLICATIONS

"Forum on Fundamental Problems in Orhtopaedic Surgery", Campbell, 1958.

"A Contoured Anterior Spinal Fixation Plate", Black et al., 1987.

"Rezaian Spinal Fixator Surgical Technique", Spinal & Orthopedic Devices, Inc.

"CASF TM Contoured Anterior Spinal Fixation System", AcroMed Corporation.

"Amset TM ALSP Anterior Locking Plate System Surgical Technique", AMS Innovation in Spine TM.

"Burst Fractures with Neurologic Deficits of the Thoracolumbar-Lumbar Spine", Kaneda et al., 1983.

"Anterior Stabilization and Decompression for Thoracolumbar Injuries", Dunn, 1986.

"Anterior Spinal Cord Decompression for Lesions of the Thoracic and Lumbar Spine, Techniques, . . . ", Kostuik, 1983.

"The Syracuse I-Plate", Bayley et al., 1990.

"Anterior Plating in Thoracolumbar Spine Injuries", Haas et al., 1990.

"Anterior Fixation for Burst Fractures of the Thoracic and Lumbar Spine with or without Neurological Involvement", Kostuik, 1987.

"The IVBF Dual-Blade Plate and Its Applications", Rao et al., 1990.

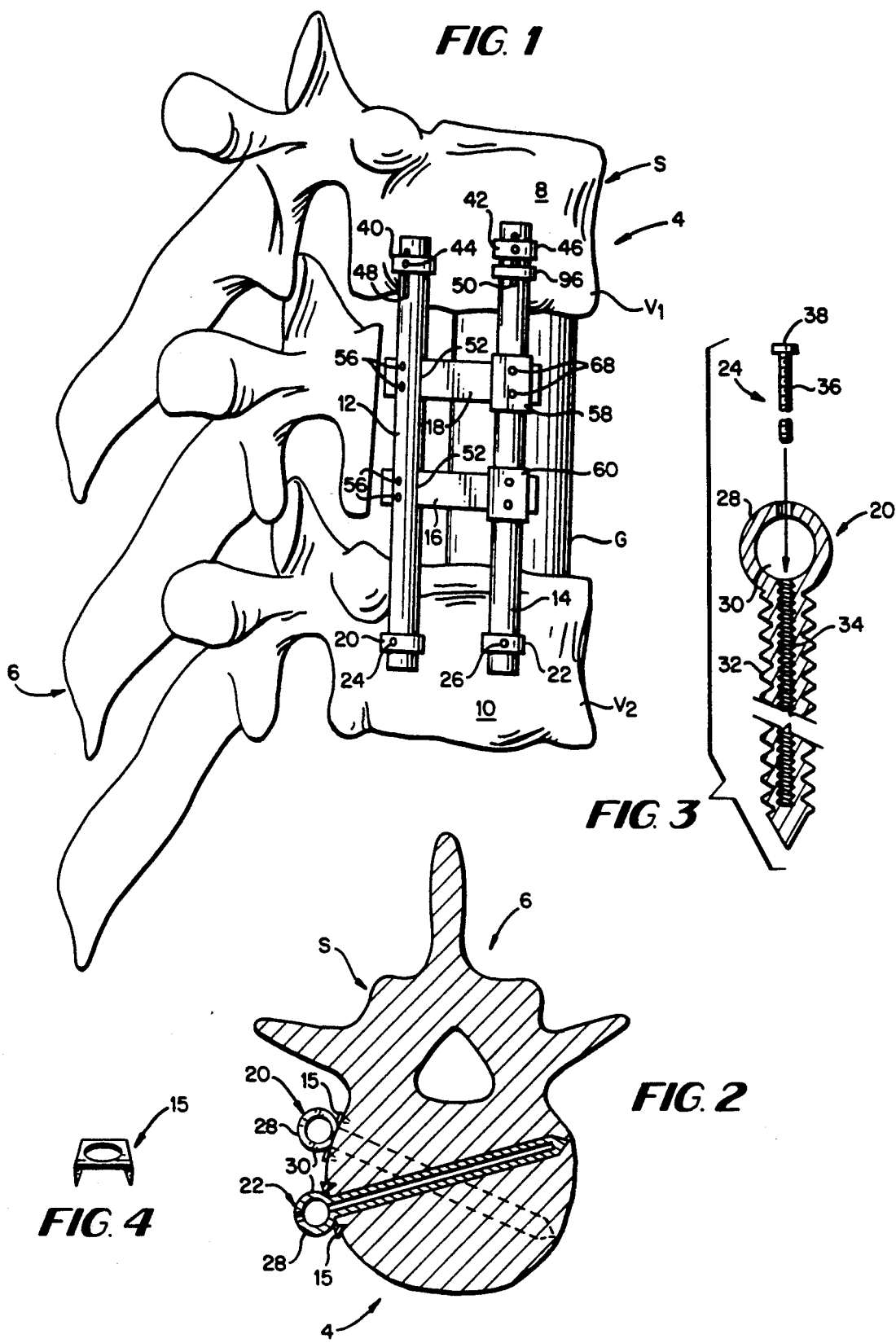

ANTEROLATERAL SPINAL FIXATION SYSTEM

This is a division of application Ser. No. 07/717,147, filed Jun. 18, 1991, now U.S. Pat. No. 5,152,303.

BACKGROUND AND SUMMARY OF THE INVENTION

The present invention relates to spinal fixation systems generally, but more particularly, to an anterolateral spinal fixation system and a related method of insertion.

Anterior spinal approaches were described in the early 1900's by Hodgson, Ito and Royle. The use of anterolateral instrumentation, however, has always been, and remains controversial for fear of neurovascular and/or mechanical complications. On the other hand, anterior approaches have recognized advantages. For example, anterolateral instrumentation and fusion techniques address directly the site of instability or deformity and avoid the need for combined or staged posterior instrumentation and fusion. In addition, anterolateral instrumentation devices immobilize fewer motion segments than standard posterior hook fixation methods. Anterolateral instrumentation can also enhance stability in burst fractures, vertebral body tumors, post traumatic kyphosis, congenital kyphosis, and anterior opening wedge lumbar osteotomies. In any case, the optimal instrumentation needs to provide immediate postoperative stability, resist failure at bone/metal interfaces, and be relatively easy and safe to insert.

As indicated above anterior and/or anterolateral devices have been used but have not been completely satisfactory. In some instances, the instrumentation lacks the necessary strength while, in others, proximity to the aorta leads to vascular problems in the form of aneurysms. Some devices do not permit independent screw placement and are usually statically locked in place after graft placement, occasionally leading to failure and oftentimes requiring further intervention.

The present invention seeks to overcome problems with prior anterolateral instrumentation by providing for independent screw placement combined with low profile instrumentation, thus avoiding the potential for device related neurologic and vascular injury; and by providing for relative movement, or dynamization, of the device after insertion, thus permitting continuous compression and load sharing and thereby avoiding microresorption.

In accordance with one exemplary embodiment of the invention, an anterolateral rod fixation device includes a pair of rods which can be fixed in substantially parallel relationship to the anterolateral vertebral body by cannulated fixation screws and associated locking screws. Upper or lower ends of the rods are provided with vertical slots to facilitate independent screw placement, and to permit relative movement between the rods and fixation screws upon removal of the locking screws. A pair of cross links are provided for rigid interconnection between the rods. Three types of cross links are contemplated for use with the fixation rods. In one version, slab-like cross links (which may be planar or slightly bent) are receivable within transverse slots provided in the rods, and rigidly secured in place by screws. In another version, sleeve-like "eyebolts" are fitted over the fixation rods, and the cross links are secured within transverse slots provided in the eyebolts. In the third version, shortened cross links are interconnected by a stepped coupling located between the fixation rods in order to accommodate the vertebral body contour without having to re-shape one or both of the fixation rods.

In accordance with another exemplary embodiment of the invention, a rod-plate fixation device includes one rod and a thin, lower profile plate in substantially parallel relationship, both of which may be fixed to the vertebral body substantially in the same manner as the double rod device of the first described embodiment. The plate offers a lower profile than the rod and, in addition, enhances stability by reason of a slightly wider stance. In this second embodiment, slab-like cross links may be secured directly to the plate, or by adaptations of the above described "eyebolts", as described in further detail hereinbelow.

In all cases, the fixation screw-bone interface may be enhanced by the utilization of four-pronged washers which are driven into the bone by the cannulated fixation screws. In addition, and as described below in greater detail, one or a pair of C-clips may be employed to limit the relative movement between and thus prevent complete distraction or separation of the fixation rods and the cannulated fixation screws.

Metals employed in the system are, of course, biocompatible, but where biodegradable components exist, they may be substituted for the metals, as will be understood by those skilled in the art.

Thus, in accordance with one aspect of the invention, there is provided an anterolateral spinal fixation system comprising a pair of substantially parallel fixation members, each provided with means for enabling varied fixation screw placement; a pair of cross links extending between the parallel fixation members, with the cross links extending through slots provided in the parallel fixation members and rigidly secured therein.

In accordance with another aspect of the invention, there is provided an anterolateral spinal fixation system comprising a pair of substantially parallel fixation members; a pair of cross links extending between the parallel fixation members; a pair of cannulated screws for each of the parallel fixation members adapted to secure the parallel fixation members to adjacent upper and lower vertebral body portions; and fastening means for rigidly securing first end portions of the fixation members to one of the upper and lower vertebral body portions, and for loosely securing second end portions of the fixation members to the other of the upper and lower vertebral body portions.

The present invention also relates to a process for insertion of the anterolateral device wherein the parallel fixation rods are initially secured at their lower ends to the lower vertebral body and, after the adjacent vertebrae on either side of an anterior portion to be replaced are separated to the extent necessary to permit insertion of the bone graft, the upper ends of the fixation rods are secured to the upper vertebral body, thus holding the adjacent vertebrae in the desired separated condition. After insertion and placement of the bone graft, the locking screws fix the upper ends of the fixation rods to the cannulated fixation screws are removed, thereby permitting relative movement between the upper fixation screws and the fixation rods which, in turn, permits continual bone graft compression during healing. As a result of this dynamization feature of the invention, solid fusion without implant failure has been achieved.

Other objects and advantages of the invention will become apparent from the detailed description which follows.

BRIEF DESCRIPTION OF THE DRAWINGS

FIG. 1 is a partial side view of a human spine with the anterior intralateral spinal fixation system of the present invention attached thereto;

FIG. 2 is a cross section of the spine shown in FIG. 1 indicating the orientation of the fixation screws utilized to attach the fixation rods to the anterolateral portion of the spine;

FIG. 3 is an exploded view, partially in section, of a threaded cannulated screw and locking screw assembly for fixing the fixation rods to the spine;

FIG. 4 is a perspective view of a four-pronged washer utilized in conjunction with the threaded cannulated screw;

DETAILED DESCRIPTION OF THE DRAWINGS

Figure 5:
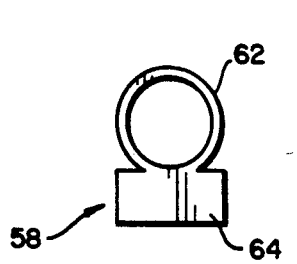
FIG. 5 is a front view of one type of cross link coupling for attaching cross links between a pair of parallel fixation rods.

With specific reference to FIGS. 1 and 2, a partial side view of the human spine S is illustrated, with the anterior of the spine indicated by reference numeral 4 and the posterior of the spine indicated by reference numeral 6. The spinal fixation system of the present invention is intended to be used primarily in surgical procedures where a bone graft G is to be inserted between adjacent vertebrae V1 and V2, the spinal fixation system to be attached to vertebral body portions 8 and 10 of the vertebrae V1, V2, respectively.

The anterolateral rod fixation system, as shown in FIG. 1, includes a pair of fixation rods 12, 14 and a pair of cross links 16, 18.

Rods 12 and 14 are fixed at their lower ends to the vertebral body 10 by a pair of cannulated screws 20, 22 and associated locking screws 24, 26, respectively. With reference to FIG. 3, the cannulated screw 20 is provided with an enlarged hollow head 28 defining an annular opening 30 sized to receive the fixation rod 12. The screw 20 is also provided with a shank portion 32 threaded on its exterior and provided with an interiorly threaded bore 34 (which can be closed at one end as shown, or open at both ends) adapted to receive the locking screw 24. The latter includes an exteriorly threaded shank portion 36 and an enlarged head 38. The cannulated screw 20 is of the self-tapping type and is adapted to be threaded directly into a pilot hole drilled into the vertebral body portion 10. The cannulated screw 22 and its associated locking screw 26 are identical and need not be further described.

The upper ends of the rods 12 and 14 are fixed to the vertebral body portion 8 by another pair of cannulated screws 40, 42 and associated locking screws 44, 46, respectively. Here again, these constructions are identical to the previously described cannulated screw 20 and associated locking screw 24.

As shown in FIG. 2, and in a preferred arrangement, the screw 20 is oriented from posterior to anterior while the cannulated screw 22 is oriented from anterior to posterior. A similar orientation may be utilized in conjunction with cannulated screws 40 and 42. It will further be appreciated that because of the sliding arrangement between the fixation rods 12 and 14, and the associated cannulated screws, the screws 20 and 22, for example, may be placed at different heights along the vertebral body portion 10 and a similar capability exists with respect to cannulated screws 40 and 42.

With reference again to FIG. 1, the locking screws 24 and 26 of the cannulated screws 20, 22, respectively, extend through bores provided in the respective rods 12 and 14, so that no relative movement is permitted between the screws 20, 22 and rods 12, 14, respectively. On the other hand, the locking screws 44, 46 of the cannulated screws 40, 42, respectively, extend through slots 48, 50, which are formed in the upper ends of the rods 12 and 14, respectively. These slots extend parallel to the longitudinal axes of the respective fixation rods and thus permit some relative sliding longitudinal movement between the rods and the cannulated screws (prior to tightening of the locking screws 44, 46), as will be explained in further detail below. To enhance the attachment of the cannulated screws to the vertebral body portions, four-pronged washers 15 as shown in FIG. 4 may be employed as shown in FIG. 2.

It should be understood that the arrangement of bores and slots in the fixation rods 12, 14 may be reversed if desired.

Figure 7:
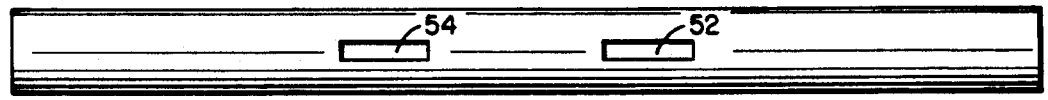
FIG. 7 is a side view of a fixation rod of the type shown on the left hand side of the device shown in FIG. 1.
Figure 8:
FIGS. 8 and 8A are perspective views of cross links which may be used in conjunction with the device shown in FIG. 1.
Figure 8A:
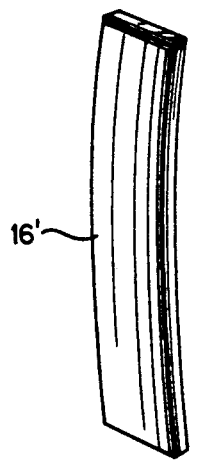

The cross links 16, 18 may be secured to the rods 12, 14 in various ways. For example, both cross links 16 and 18, which may comprise thin identical plate-like members having rectangular cross sections and which may be planar (as shown at 16 in FIG. 8) or slightly bent (as shown at 16' in FIG. 8A), may be received within correspondingly shaped, transverse apertures or slots 52, 54 formed at longitudinally spaced locations along the rod 12 (see FIG. 7) and secured thereto by means of interference fit bolts 56 which may be, for example, conventional Allen type screws, or the like. It will be appreciated that the cross links in this arrangement lie generally within an area defined in part by the diameters of the rods. This provides a very low profile device with minimal intrusion of surrounding areas.

Figure 6:
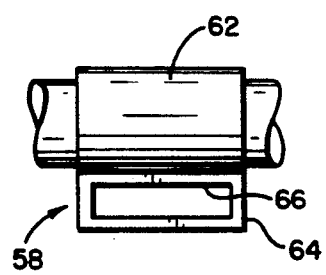
FIG. 6 is a side view of the cross link coupling shown in FIG. 5.

A second manner of attachment of the cross links 16, 18 to an associated fixation rod is shown on the right hand side of FIG. 1 where cross link couplings 58 and 60 are slidably received on the rod 14. Since these couplings are identical, only one need be described in detail. Referring now to FIGS. 5 and 6, coupling 58 is formed with a sleeve-like body portion 62 which is sized to slide along the rod 14, and it will be appreciated that the body portion 62 can be fixed along the length of the rod 14 at the desired location by set screws or the like. The coupling 58 also includes a transversely oriented upper portion 64 provided with a through slot 66 extending perpendicular to the sleeve portion 62 and rod 14. As best seen in FIG. 1, the cross link 18 may be slidably received within the transverse slot 66 and fixed thereto by means of, for example, set screws 68. The cross link 16 may be attached to the fixation rod 14 in a similar manner. It will be appreciated, of course, that the coupling arrangement as between rods 12, 14 and associated cross links 16, 18 will normally be identical at all four points of attachment, although this need not be the case.

Figure 6A:
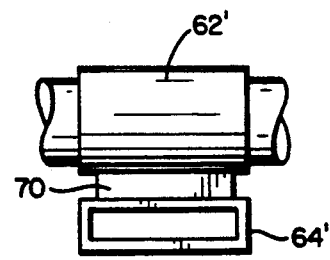
FIG. 6a is a side view of a variation of the cross link coupling shown in FIG. 6.

FIG. 6a illustrates an alternative embodiment of the coupling 58 where the upper slotted portion 64' is raised relative to the sleeve portion 62' by a vertically extending flange 70. It will be appreciated by those of ordinary skill in the art that different height flanges 70 may be utilized to raise the anterior cross link height to the posterior cross link height, depending on the contour of the vertebral body portions.

Figure 9:
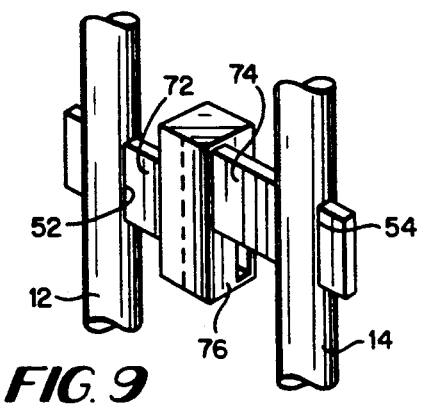
FIG. 9 is a partial perspective view of a second type of cross link and cross link coupling which may be utilized in the device shown in FIG. 1.
Figure 10:
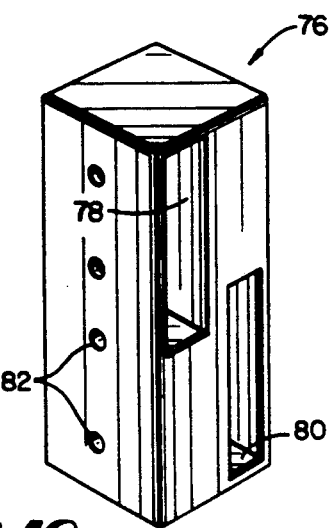
FIG. 10 is an enlarged perspective view of the cross link coupling shown in FIG. 9.

An alternative cross link arrangement is illustrated in FIG. 9 where the rods 12 and 14 each receive a partial cross link 72, 74 which are connected intermediate the rods 12 and 14 by a "stacked domino" type coupling member 76. As best seen in FIG. 10, the coupling 76 is provided with diagonally oriented through slots 78 and 80 which are adapted to receive the cross links 72, 74, the latter being locked in place by set screws or other suitable means, via holes 82. This coupling arrangement is particularly advantageous when the rods 12 and 14 do not lie in the same plane due to variations in the contour of the vertebral body.

Figure 11:
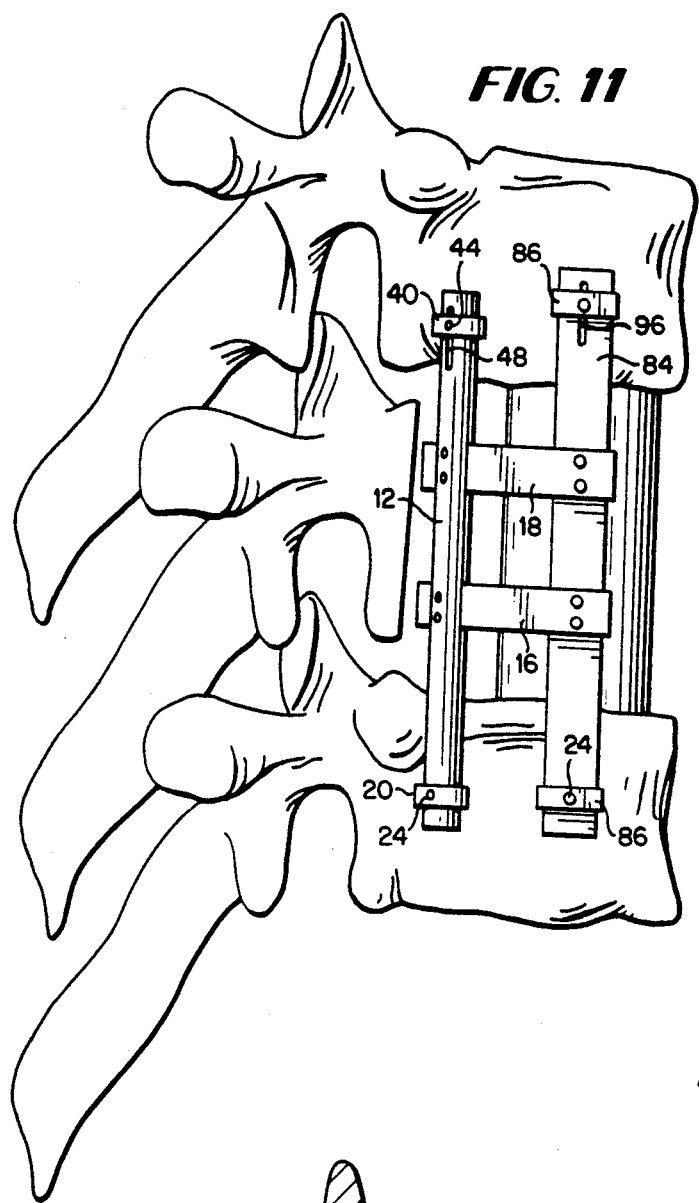
FIG. 11 is a side view of a second embodiment of the anterior anterolateral spinal fixation system in accordance with the invention.
Figure 13:
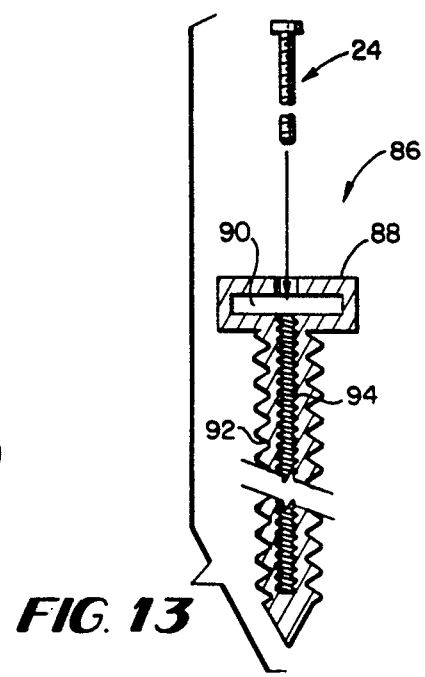
FIG. 13 is an exploded view, partially in section, of a cannulated screw of the type utilized to fix the anterior plate shown in FIG. 11 to the spine.
Figure 12:
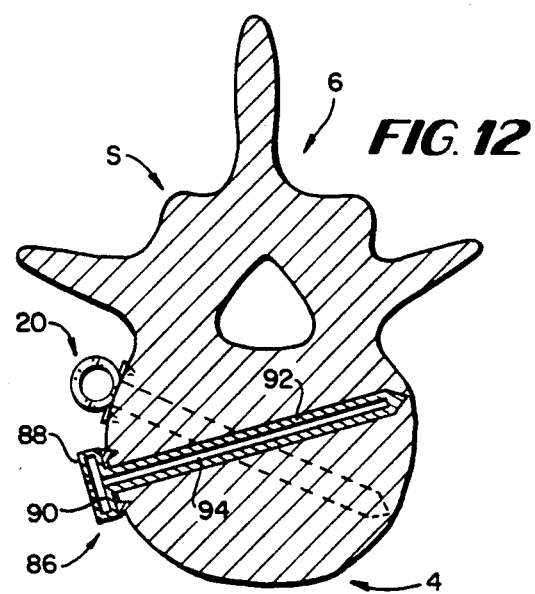
FIG. 12 is a cross section of the spine shown in FIG. 1 indicating the orientation of the fixation screws which attach the device shown in FIG. 11 to the spine.

Turning now to FIG. 11, a second exemplary embodiment of the invention is illustrated wherein the anterolateral spinal fixation system includes a fixation rod 12 and an associated fixation plate 84 extending parallel thereto. The plate 84 may be a thin plate of rectangular cross section which, of course, necessitates modifications of the various system components which are utilized in conjunction therewith. For example, cannulated screws 86 and 88 are each provided with enlarged head portions which are designed to accommodate the rectangular cross section of the fixation plate 84. With reference to FIGS. 12 and 13, the cannulated screw 86 (cannulated screw 88 is identical) includes an enlarged head portion 88 provided with an anterior through slot 90 which has a rectangular shape adapted to slidably receive the fixation plate 84. The screw 86 also includes a threaded shank portion 92 and an interiorly threaded bore 94 which is adapted to receive a locking screw 24 as described hereinabove. As best seen in FIG. 11, the lower ends of the rod 12 and plate 84 are fixed to the vertebral body portion in the same manner as described above in connection with the embodiment illustrated in FIG. 1. At the same time, the upper end portions of the rod 12 and fixation plate 84 are also fixed in the same manner as described above, plate 84 being provided with a through-slot 96 similar to slots 48, 50.

It will be understood that a pair of fixation members, each having the cross-sectional shape of plate 84 may also be employed, in conjunction with a pair of cross links.

Cross links 16 and 18 may be secured directly to the flat surface of the plate 84 by set screws or the like (as shown in FIG. 11) or, alternatively, an "eyebolt" type coupling of the type shown in FIG. 5 may be utilized with the understanding that the sleeve-like portion would be altered accommodate the rectangular cross section of the plate 84. It will further be appreciated that the stacked domino type coupling 76 as described above in conjunction with cross link elements 72, 74 and as shown in FIGS. 9 and 10 may also be utilized with the FIG. 11 embodiment.

Figure 14:
FIGS. 14 and 14a are side views of locking C-rings for attachment to a fixation rod and fixation plate, respectively.
Figure 14A:

In both embodiments illustrated in FIGS. 1 and 11, the extent of relative sliding movement between the upper cannulated screws and the fixation rods (or fixation plate) may be limited by the utilization of an appropriately shaped C-clip. For circular rods such as shown at 12 and, 14, a circular C-clip 98 may be utilized, as best seen in FIG. 14. For a fixation plate such as shown at 84, a rectangular C-clip 100 may be employed. Clips 98, 100 may be secured to a fixation rod or plate by means of set screws or the like.

The manner in which the spinal fixation system of the present invention may be used in a surgical procedure to insert a bone graft G between adjacent vertebrae V1, V2 will now be described. It will be appreciated that while described in conjunction with the embodiment illustrated in FIG. 1, the process itself will not differ in any significant respect when utilizing the system illustrated in FIG. 11.

After connection of the fixation rods 12 and 14 to the vertebral body portion 10 of the vertebra V2, at desired locations therealong, the upper ends of the fixation rods 12 and 14 will be loosely associated with the cannulated screws 40, 42, also independently placed in the desired locations along the vertebral body portion 8 of the vertebra V1. Cross links 16 and 18 are then secured between the fixation rods 12 and 14 as previously described. Separation of the vertebra V1 and V2 to the extent required for the insertion of the bone graft G is then effected by any conventional methodology. After the vertebra V1 and V2 have been separated, the locking screws 44 and 46 will be inserted and tightly screwed in place to preclude any further relative movement of the fixation rods 12 and 14 and cannulated screws 40 and 42. At the same time, of course, the vertebra V1 and V2 are now rigidly held in the desired separated position, thereby permitting insertion of the bone graft G. After insertion of the bone graft G, the locking screws 44 and 46 may be removed thereby permitting relative sliding movement between the cannulated fixation screws 40, 42 and rods 12 and 14 which, in turn, permits natural compression of the bone graft G by the vertebrae V1 and V2. The C-clips 98 and/or 100 will allow a limited degree of axial movement between the cannulated screws 40 and 42 and the respective fixation rods 12 and 14 but are located to preclude complete separation of the fixation rod from the cannulated screw.

The above described anterolateral rod and rod/plate fixation systems are designed to permit independent placement of the fixation screws, to provide a low profile through the use of specially designed cross links and cross link couplings, and to permit continuous impaction on the bone graft to thereby avoid microresorption thus eliminating fixation device failures.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A dynamic anterolateral spinal fixation system comprising:
 a pair of substantially parallel elongated fixation members, each provided with means for enabling varied fixation screw placement;
 a pair of fixation screws for each of said fixation members, adapted to cooperate with said enabling means for attaching opposite ends of each of said fixation members to upper and lower vertebral body portions on an anterolateral side thereof, and wherein said enabling means permits movement of said fixation members in a longitudinal direction of said fixation member relative to one or more of said screws at one of said opposite ends of said fixation members, after said screws have attached said opposite ends of each of said fixation members to the upper and lower vertebral body portions;
 a pair of cross link plates extending between said parallel fixation members;
 said cross link plates extending through slots provided in said parallel fixation members and rigidly secured therein.

2. A spinal fixation system according to claim 1 wherein each of said fixation screws has an enlarged head portion and a threaded shank portion, said enlarged head portion formed with an aperture corresponding to a cross sectional shape of said parallel fixation members, and wherein each fixation member is slidably received at said opposite ends in the apertures of a respective pair of said screws.

3. A spinal fixation system according to claim 2 wherein said enabling means comprises an elongated slot in each of said fixation members, said slots extending axially along said fixation members at said opposite ends thereof.

4. A spinal fixation system according to claim 3 wherein each of said fixation screws includes an associated locking screw adapted to extend through said enlarged head and said elongated slot and into said threaded shank portion.

5. A spinal fixation system according to claim 1 wherein said cross link plates are rigidly secured within said slots by screws.

6. A spinal fixation system according to claim 3 wherein said enabling means are located at only one of said opposite ends of each of said fixation members.

7. A dynamic anterolateral spinal fixation system for attachment to upper and lower anterolateral vertebral body portions comprising:
 a pair of substantially parallel, elongated fixation members having a pair of transverse cross link plates extending therebetween, each fixation member having fastening apertures at first and second opposite ends thereof, said apertures at said first ends comprising round holes and said apertures at said second ends comprising elongated slots;
 a pair of attachment screws for attaching each of said pair of fixation members to the upper and lower anterolateral vertebral body portions, each attachment screw having an enlarged head portion and a shank portion, said enlarged head having an aperture sized to slidably receive a respective one of said fixation members, said shank portion having an externally threaded surface; and
 a locking screw for each said attachment screw, said locking screw adapted to extend through a respective enlarged head portion, and a respective fastening aperture in a respective fixation member; and wherein said fastening apertures at said first ends of said fixation members prevent relative axial movement between said attachment screws at said first ends and said fixation members, and further wherein said fastening apertures at said second ends of said fixation members permit relative axial movement between said attachment screws at said second ends and said fixation members.

8. The dynamic anterolateral spinal fixation system of claim 7 wherein each fixation screw is formed with an interiorly threaded bore in said shank portion which is adapted to receive a threaded portion of a respective locking screw.

9. The spinal fixation system according to claim 7 wherein said pair of fixation members includes at least one elongated cylindrical rod.

10. The spinal fixation system according to claim 7 wherein said pair of fixation members includes at least one, elongated plate.

11. The spinal fixation system according to claim 7 wherein said pair of cross link plates are received in respective slots provided in said fixation members.

12. The spinal fixation system according to claim 7 wherein said pair of cross link plates extend between coupling members slidably received on said fixation members.

13. The spinal fixation system according to claim 7 wherein said cross link plates each comprise two portions interconnected by a coupling located between said fixation members.

14. The spinal fixation system according to claim 7 wherein at least one of said fixation members comprises a rod having a circular cross section.

15. The spinal fixation system according to claim 14 wherein said cross link plates are received within apertures of similar cross-sectional shape provided in said at least one rod.

16. The spinal fixation system according to claim 14 wherein said cross link plates are received in coupling members mounted to said at least one rod.

17. The spinal fixation system according to claim 7 wherein at least one of said fixation members comprises an elongated plate having a substantially rectangular cross section.

18. The spinal fixation system according to claim 17 wherein said cross link plates are attached at first ends to said at least one elongated plate in flush engagement therewith.

* * * * *